United States Patent [19]

Oh

[11] Patent Number: 4,795,469
[45] Date of Patent: Jan. 3, 1989

[54] THREADED ACETABULAR CUP AND METHOD

[76] Inventor: Indong Oh, 851 Lyndon St., South Pasadena, Calif. 91030

[21] Appl. No.: 889,187

[22] Filed: Jul. 23, 1986

[51] Int. Cl.⁴ .............................................. A61F 2/34
[52] U.S. Cl. .................................................... 623/22
[58] Field of Search ...................... 623/22, 23, 16, 18, 623/20, 21; 403/4, 90, 125, 135, 140

[56] References Cited

U.S. PATENT DOCUMENTS

| | | | |
|---|---|---|---|
| Re. 31,865 | 4/1985 | Roux | 623/22 |
| 3,903,549 | 9/1975 | Deyerle | 623/22 |
| 4,437,193 | 3/1984 | Oh | 623/22 |
| 4,623,351 | 11/1986 | Church | 623/22 |
| 4,623,352 | 11/1986 | Oh | 623/23 |
| 4,650,491 | 3/1987 | Parchinski | 623/22 |
| 4,662,891 | 5/1987 | Noiles | 623/22 |

Primary Examiner—Richard J. Apley
Assistant Examiner—Alan W. Cannon
Attorney, Agent, or Firm—Gordon L. Peterson

[57] ABSTRACT

An acetabular cup comprising a shell having inner and outer ends, a cavity having an outer opening at the outer end, a surface defining an inner opening at the inner end and external screw threads for threading the shell into the acetabulum and an insert having an external polar cap and a concave bearing surface of generally part spherical configuration opening at a mouth. The insert is adapted to receive a femoral head and has an overhang to reduce the likelihood of dislocation. The insert is receivable in the shell with the polar cap being received in the inner opening of the shell. Interlocking teeth on the surface of the shell and on the polar cap of the insert hold the insert in any of a plurality of different angular positions relative to the shell so that the desired angular orientation of the overhang can be obtained.

16 Claims, 4 Drawing Sheets

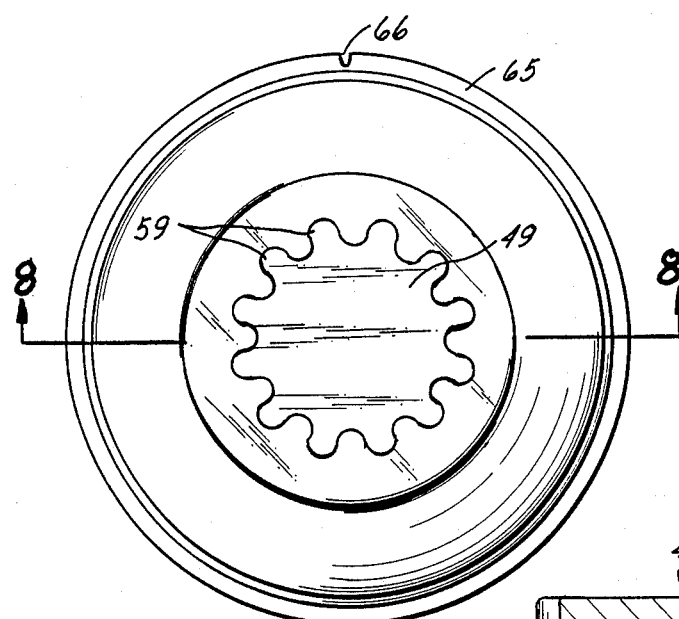
FIG.7
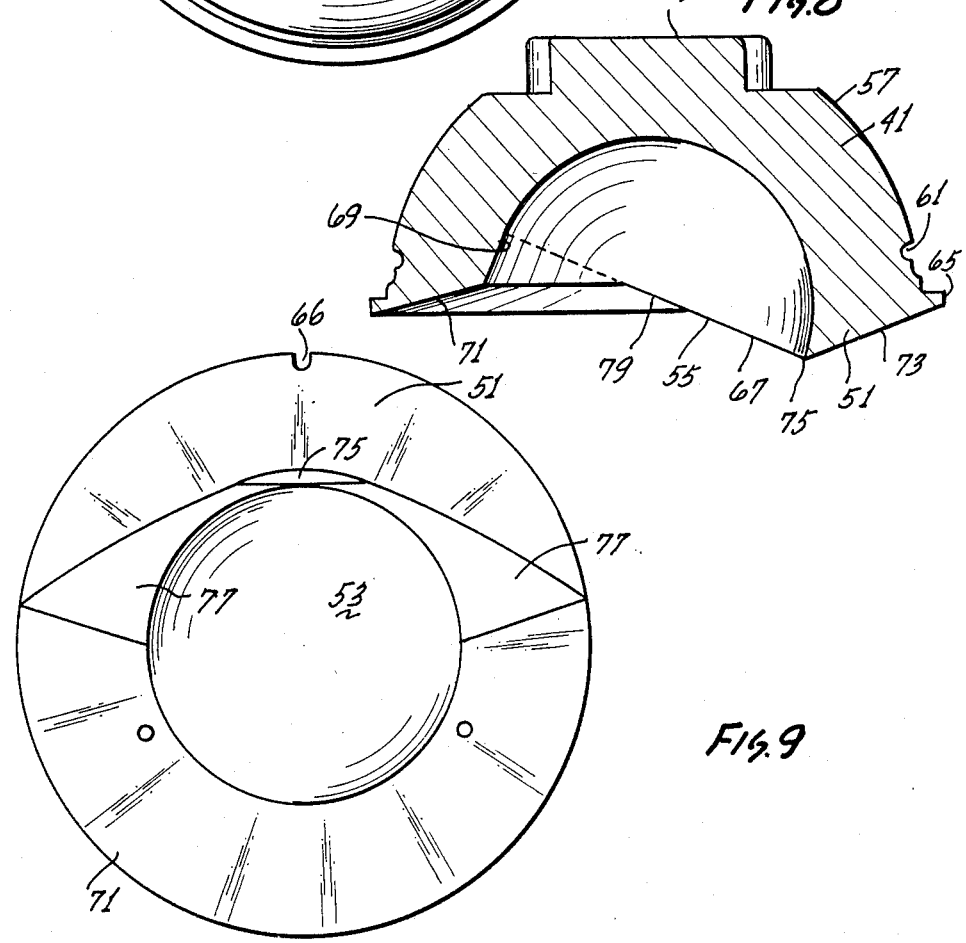
FIG.8
FIG.9

THREADED ACETABULAR CUP AND METHOD

BACKGROUND OF THE INVENTION

A hip joint comprises a socket or acetabulum and a femoral head or ball received in the acetabulum. Thus, the hip joint is a ball and socket joint which provides universal motion.

Various diseases, such as osteoarthritis attack the hip joint, and when this occurs, it may be necessary to use an appropriate hip joint prosthesis to replace the femoral head and/or the acetabulum. One form of acetabular prosthesis is an acetabular cup which includes a threaded shell and an insert receivable in the shell. The threaded shell has the advantage that it can be threaded into the acetabulum thereby eliminating the need for cement.

In an acetabular cup of this type, the insert may be provided with an overhang to resist dislocation of the hip joint. The overhang extends circumferentially for less than 360°. To allow the surgeon to select the most advantageous angular orientation of the overhang, it is known to provide the shell and the insert with a "dial-in" feature. The "dial-in" feature may be implemented, for example, by a lug on the shell and corresponding recesses in the insert.

The shell is commonly threaded into the acetabulum using a tool which may engage, for example, holes or lugs in the rim of the threaded shell. One disadvantage of this arrangement is that the driving connection between the tool and the shell is remote from the leading end of the shell thereby making the threading of the shell into the acetabulum somewhat more difficult to control. When used with the "dial-in" feature, this construction is made more complex in that driving surfaces are required on the cup for threading of the cup into the acetabulum and to provide the "dial-in" feature. In addition, in some prior art devices, the "dial-in" feature provides quite limited dialing increments of, for example, 45° to 60°.

SUMMARY OF THE INVENTION

This invention provides an acetabular cup which overcomes these disadvantages. With this invention, the driving force to the threaded shell is applied near the leading end of the shell so that better control over the implantation of the shell is obtained. In addition, construction is simplified in that the same driving surface on the shell is used for both turning the shell into the acetabulum and for the "dial-in" feature. Also, a large number of dialing increments can be obtained with the acetabular cup of this invention.

The acetabular cup of this invention includes a shell and an insert. The shell has inner and outer ends, a cavity defining an opening at the outer end and a surface defining an inner opening at the inner or leading end. External screw threads are provided for threading the shell into the acetabulum by rotation of the shell generally about a rotational axis which extends between inner and outer ends.

The insert has an external polar cap and a concave bearing surface of generally part spherical configuration opening at a mouth with the bearing surface being adapted to receive a femoral head and slidably cooperate therewith. The insert has an overhang and is receivable in the cavity of the shell with the polar cap being received in the inner opening of the shell.

With this invention, a "dial-in" feature is provided by interlocking means on the polar cap of the insert and on the surface of the shell which defines the inner opening at the inner end. The interlocking means holds the insert in any of a plurality of different angular positions relative to the shell so that a desired angular orientation of the overhang in the frontal and sagittal planes can be selected.

The portion of the interlocking means which is on the shell constitutes a driven surface. This driven surface can cooperate with a tool to screw the shell into the acetabulum. The driven surface of the shell also forms a portion of the interlocking means and, therefore, provides a dual function which reduces the complexity of the acetabular cup. In addition, because the driven surface is at the inner or leading end of the shell, it enables the force of threading the shell into the acetabulum to be applied to the shell near the leading end of the shell so that better control of this operation can be obtained.

In a preferred construction, the interlocking means comprises a plurality of interlockable gear teeth on the shell and the insert. The gear teeth enable many dialable increments to be provided and they efficiently transmit the threading forces to the shell.

Rotating the insert to select the desired angular position of the overhang, i.e. using the "dial-in" feature of this invention does not move the center of the bearing surface regardless of the angular position which is selected. Moreover, with this invention, the center of the bearing surface can be substantially coincident with the center of the metal shell and the natural acetabulum.

In order that the shell can be retained entirely within the acetabulum, it preferably extends for no more than a hemisphere. The shell preferably has at least one port leading to the cavity. The port can be used for viewing during the surgery and for bone graft, if desired, to enhance the stability of the prosthesis in the acetabulum. To facilitate reduction, i.e. placement of the femoral head into the acetabular cup during surgery, the circumferential extent of the overhang is reduced to no more than, and preferably less than, 180°. The height of the overhang is also minimized.

Another feature of this invention is that the insert can be removed from the shell in a subsequent surgery with relative ease and without having to remove the threaded shell. This can be accomplished, for example, if the insert is releasably locked to the shell and whether or not the "dial-in" and other features of this invention are present.

To remove the insert, a tool holder is placed against the shell and a removal tool is placed in the tool holder with the removal tool engaging the insert. The insert can then be removed by rotating the removal tool in the tool holder while the removal tool is engaging the insert. More specifically, the removal tool may have a threaded distal tip which is received within an opening in a polar region of the insert so that rotation of the removal tool removes the insert from the shell against the restraint of the releasable lock which tends to retain the insert in the shell.

The invention together with additional features and advantages thereof may best be understood by reference to the following description taken in connection with the accompanying illustrative drawings.

BRIEF DESCRIPTION OF THE DRAWINGS

FIG. 7 is a top plan view of the insert.

FIG. 8 is a sectional view taken generally along line 8—8 of FIG. 7.

FIG. 9 is a bottom plan view of the insert.

DESCRIPTION OF THE PREFERRED EMBODIMENT

Figure 1:
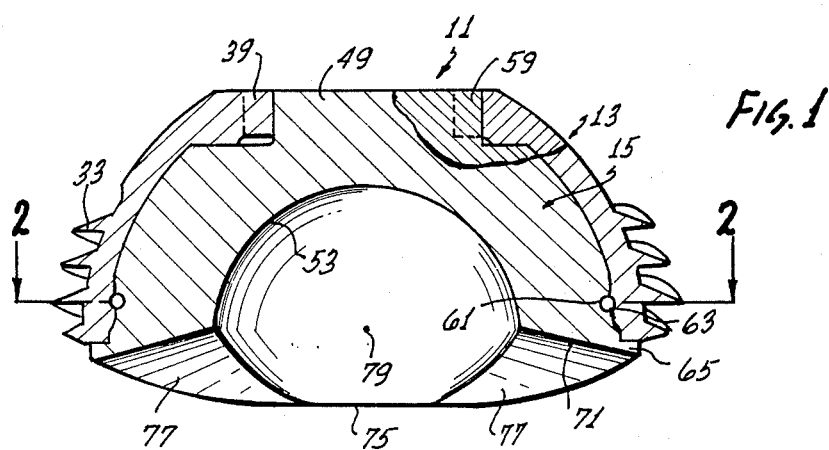
FIG. 1 is an axial sectional view of a threaded acetabular cup constructed in accordance with the teachings of this invention.
Figure 2:
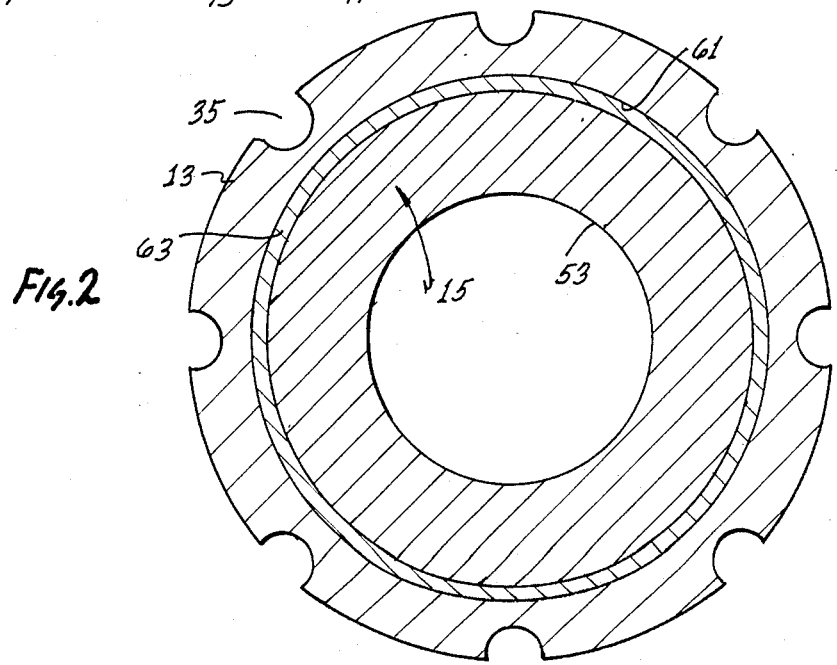
FIG. 2 is a sectional view taken generally along line 2—2 of FIG. 1.
Figure 4:
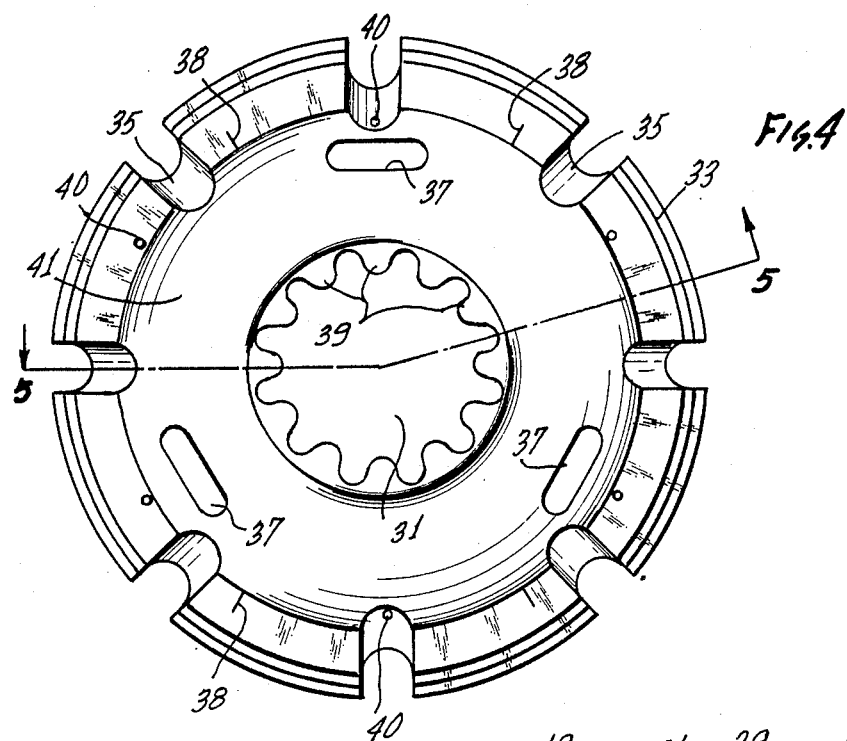
FIG. 4 is a top plan view of the shell.
Figure 5:
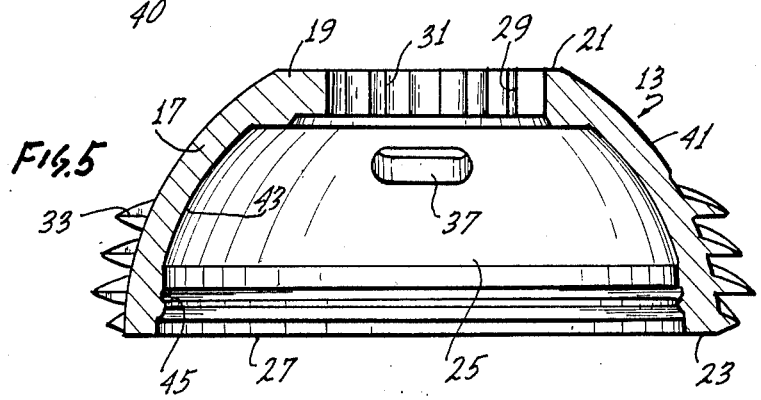
FIG. 5 is a sectional view taken generally along line 5—5 of FIG. 4.
Figure 6:
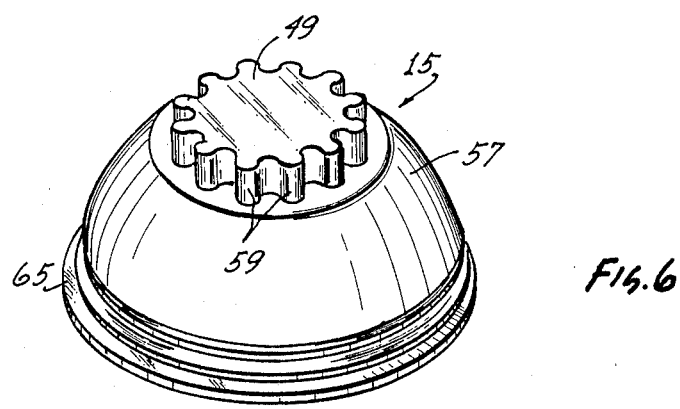
FIG. 6 is a perspective view of one form of insert.

FIG. 1 shows a threaded acetabular cup 11 which comprises a shell 13 and an insert 15. The shell 13 (FIGS. 3-5) is preferably constructed of a metal such as titanium, and includes a peripheral wall 17, and an end wall 19 integral with the peripheral wall, an inner end 21, an outer end 23, a cavity 25 having an outer opening 27 at the outer end 23 and a driven surface 29 defining an inner opening 31 at the inner end 21. The shell 13 has external screw threads 33, which are interrupted along grooves 35 to make the threads self tapping. A plurality of ports 37 (3 being illustrated) are provided in the peripheral wall 17 axially inwardly of the threads 33.

The driven surface 29 defines a plurality of gear teeth 39 located around the inner opening 31. In the embodiment illustrated, 12 of such teeth are provided. Indicia 38 and 40, which are different from each other and which may be formed by machining, are provided in radial alignment with alternate gear teeth 39.

The shell 13 is a one piece integral member which has an outer surface 41 which is generally in the form of a hemisphere which has been truncated along the end wall 19. The hemispherical configuration of the outer surface 41 minimizes the bone that must be removed for implanting of the shell and the truncation of the shell makes the shell more stable in the acetabulum where bone grafting is added. The shell 13 has a truncated hemispherical inner surface 43 and a groove 45 (FIG. 5) in the inner surface 43 adjacent the outer opening 27. Of course, the groove 45 and the threads 33 upset the generally hemispherical nature of the inner surface 43 and the outer surface 41.

The insert 15 (FIGS. 6-9) is a one piece member which is preferably constructed of a biocompatible low friction, wear resistant material. In this embodiment the material is polyethylene. The insert 15 has a peripheral wall 47 and is generally in the form of a hemispherical cup having a polar cap 49 and an overhang 51. The insert 15 has a concave bearing surface 53 of hemispherical configuration opening at a mouth 55. The bearing surface 53 is adapted to receive a femoral head (not shown) and slidably cooperate therewith.

The insert 15 has an outer surface 57 which is shaped to be received within the cavity 25 of the shell 13 and to conform to the inner surface 43 of the shell as shown in FIG. 1. The periphery of the polar cap 49 defines gear teeth 59 which, like the teeth 39, preferably have a rounded configuration to minimize the likelihood of point contact which would create "play" in the gears. The polar cap 49 is receivable within the inner opening 31 of the shell 13 with the gear teeth 59 meshing with the gear teeth 39 as shown in FIG. 1. The outer surface 57 has an annular groove 61 which cooperates with the groove 45 of the shell to provide a space for an annular locking or retaining ring 63 (FIG. 1) which releasably retains the insert within the shell. The insert 15 has an annular flange 65 around its base and indicia or a marker in the form of a groove or notch 66 in the flange.

The bearing surface 53 is hemispherical and terminates at a plane 67 (FIG. 8). The insert 15 has a surface 69 of part cylindrical configuration which extends from one end of the plan 67 to a conical surface 71 which extends radially outwardly and axially away from the polar cap 49 to the outer surface 57. As shown in FIG. 9, the conical surface 71 extends for just over 180° around the bearing surface 53. The surface 69 is not a functional surface in terms of slidable cooperation with the femoral head.

The overhang 51 extends for less than 180° as shown in FIG. 9. More specifically, the overhang 51 is defined by a conical surface 73 which extends from the outer surface 57 radially inwardly and axially away from the polar cap 49 all the way to the bearing surface 53. If desired, the conical surface 73 may blend into a small flat 75 at the bearing surface 53. The conical surface 73 extends for less than 180° as shown in FIG. 9 and terminates radially inwardly at the plane 67 along flat surfaces 77 (FIG. 9) which lie in the plane 67. This construction provides the overhang 51 with the desired ability to resist dislocation while facilitating reduction and providing a good range of motion.

Figure 3:
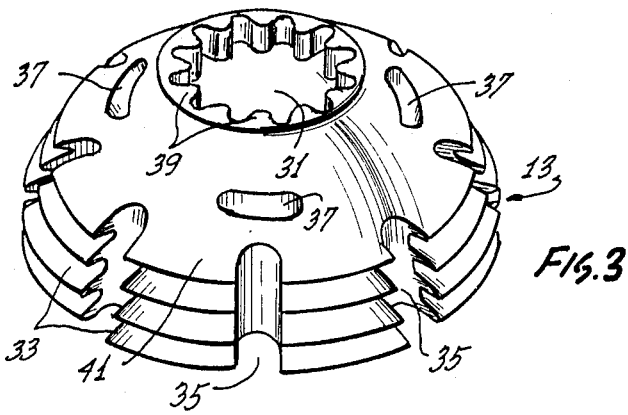
FIG. 3 is a perspective view of one form of threaded shell.

The bearing surface 53 has a center 79 (FIGS. 1 and 8). The center 79 is also the center of the part-hemispherical inner and outer surfaces 43 and 45 of the shell 13 when the insert is releasably retained within the shell by the locking ring 63 as shown in FIG. 3.

Figure 10:
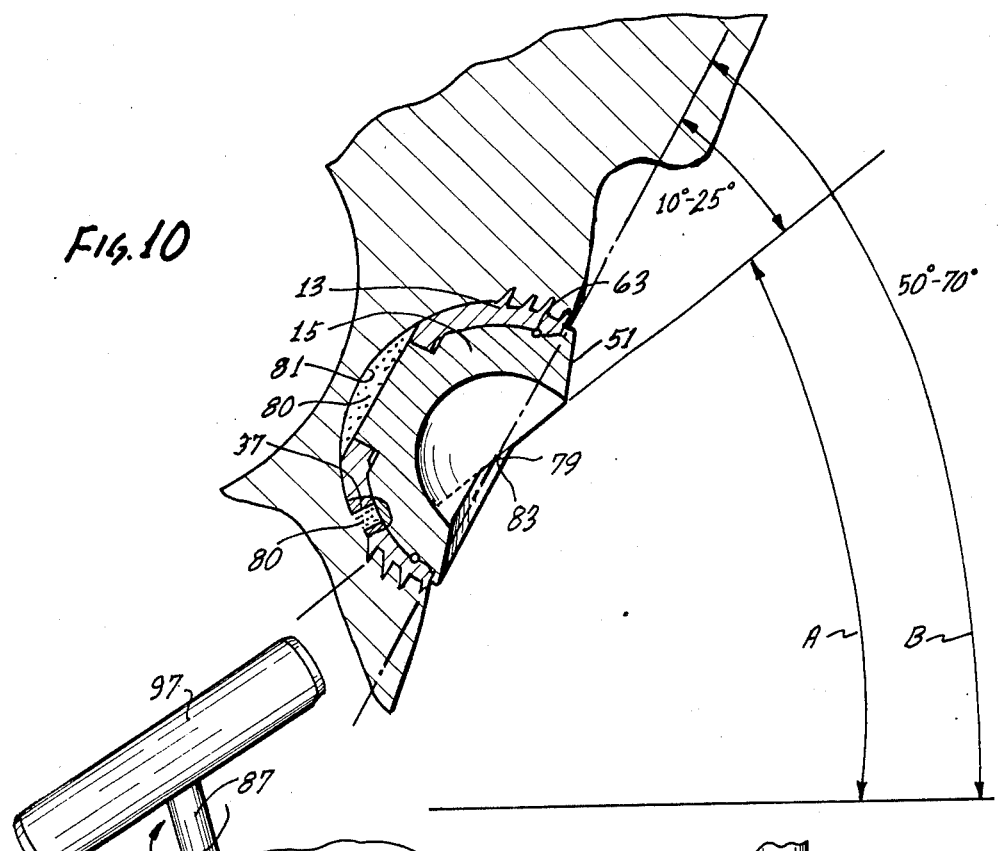
FIG. 10 is a sectional view on a frontal plane showing the threaded acetabular cup implanted in an acetabulum.

The acetabular cup 11 can be implanted into an acetabulum 81 as shown in FIG. 10. More specifically, the acetabulum 81 is prepared in a conventional manner and the shell 13 is then threaded into the acetabulum. To accomplish this, a tool (not shown) having a gear configuration adapted to be received within the inner opening 31 and mesh with the gear teeth 39 is used to screw the shell into the acetabulum by rotating the shell about a rotational axis 82 (FIG. 10). This applies the driving force to the shell 15 at its leading or inner end 21 so that better control can be obtained for this operation. The shell 13 is completely threaded into the acetabulum 81 so that essentially none of the peripheral wall 17 of the shell 13 protrudes out of the acetabulum 81. During the insertion of the shell 13, the surgeon can observe the progress of the threading operation through the ports 37, and if the tool is removed from the inner opening 31, that opening can also be used to make sure that the shell is correctly placed within the acetabulum 81. If desired, the inner opening 31 and ports 37 can also be used for bone graft material 80 (FIG. 10) to improve the fixation of the shell in the acetabulum.

Next a trial insert (not shown) which may be essentially identical to the insert 15, is placed into the shell 13 with the surgeon selecting the desired angular orientation for the overhang 51. Usually, it is desired to position the overhang 51 in the superior-posterior region. The surgeon notes which of the indicia 38 and 40 is aligned with the notch 66 of the trial insert in the desired angular orientation. The trial insert is then removed, and the insert 15 is inserted into the shell in the same angular position by aligning the notch 66 of the insert 15 with the same one of the indicia 38 and 40 that the notch of the trial insert was previously aligned with. Because the indicia 38 and 40 have different appearances, it is much easier for the surgeon to remember which of the 12 angular positions the notch of the trial insert was pointing at. The insert 15 is retained within the shell 13 by the retaining ring 63.

When implanted as shown in FIG. 10, the center 79 coincides with the center 83 of the acetabulum 81 and the rotational axis 82 passes through the centers 79 and 83. The abduction angle A may be, for example, 40° whereas the natural abduction angle B may range from 50° to 70° with 60° being a typical approximation. Keeping the same center of rotation of the natural acetabulum and prosthetic acetabular components is important in regard to the optimal joint force and force direction. To achieve this biomechanical feature, and to reduce the incidence of dislocation of the femoral head prosthesis, a capacity to provide an overhanging bearing surface at a strategic orientation is important. To do so the bearing surface is rotated 10°-25° toward a horizontal plane while keeping the same center of rotation. Reducing the abduction angle reduces the likelihood of dislocation by giving optimal coverage of the femoral head by the bearings surface 53 in the frontal and sagittal planes. Contrary to this, if the center of rotation were moved outward, it would increase the body weight moment arm and decrease the abductor moment arm. Thus, the resultant joint load would increase and the joint force would be directed outwardly, making it possible to loosen the acetabular component fixation. Furthermore, the use of a large or prominent overhang 51 would make reduction of the femoral head prosthesis extremely difficult. The cup 11 may be used with a prosthetic femoral component as shown, for example, in Oh U.S. Pat. No. 4,437,193.

Figure 11:
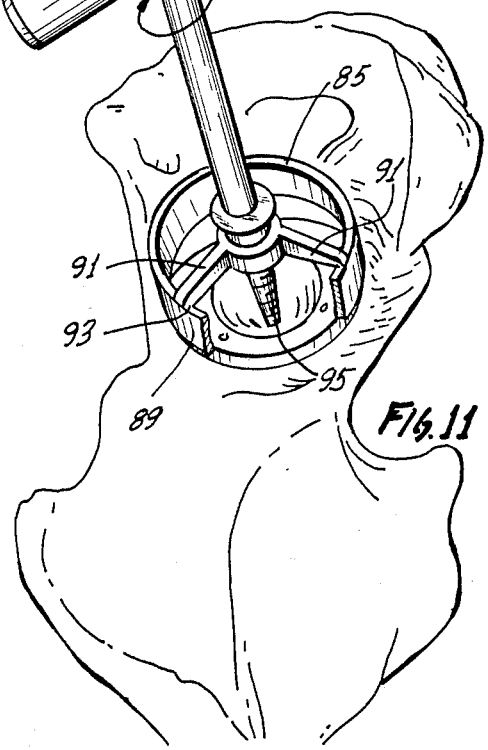
FIG. 11 shows a preferred method and apparatus for removing the insert from the shell.
Figure 12:
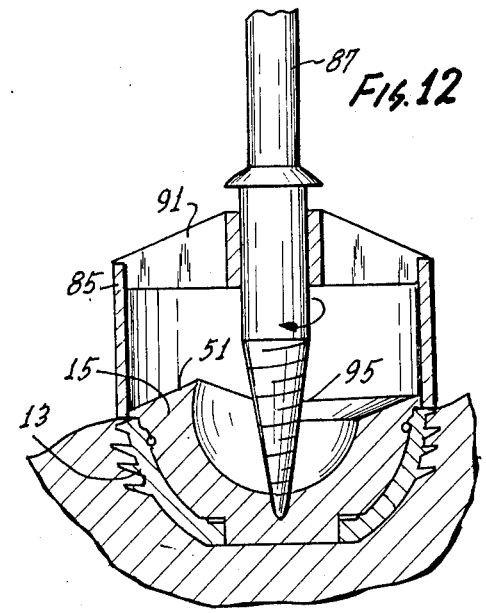
FIG. 12 is a sectional view showing removal of the insert from the shell.

Another feature of this invention is the removal of the insert 15 from the shell 13 to permit another insert 15 to be implanted in the same shell in a subsequent surgery. This can be accomplished as shown by way of example in FIGS. 11 and 12. This can be accomplished using a tool holder 85 and a removal tool 87. The tool holder 85 includes a ring 89, radially extending arms 91 and a bearing 93 retained at the center of the ring by the arms 91. The tool holder 85 can be placed with the ring 89 against an exposed portion of the base of the shell 13 as shown in FIG. 12. The tool holder can then be used to support a drill for forming a small hole in a polar region of the. insert 15. For example, the hole or opening may extend completely through a central region of the polar cap 49. Thereafter, the removal tool 87 is placed within the bearing 93 as shown in FIGS. 11 and 12. A distal region of the removal tool has screw threads 95 and a handle 97 is provided at the proximal end of the tool. By rotating the removal tool 87 with the threads 95 engaging the insert 15 at the opening, the removal tool is threaded into the insert 15 to withdraw the insert from the shell 13 against the force of the retaining ring 63, which releasably retains the insert in the shell. Thereafter another insert, which may have some different characteristics, can be installed in the shell 13.

Although an exemplary embodiment of the invention has been shown and described, many changes, modifications and substitutions may be made by one having ordinary skill in the art without necessarily dearting from the spirit and scope of this invention.

I claim:

1. An acetabular cup which can be implanted in the acetabulum comprising:
   a shell having inner and outer ends, a cavity having an outer opening at said outer end and a surface defining an inner opening at said inner end and at a polar region of the shell, external screw threads for threading the shell into the acetabulum by rotation of the shell generally about a rotational axis which extends between said inner and outer ends:
   an insert having an external polar cap and a concave bearing surface of generally part spherical configuration opening at a mouth, said bearing surface being adapted to receive a femoral head and slidably cooperate therewith, said insert being receivable in the cavity of the shell with the polar cap being received in the inner opening of the shell
   said insert ahving an overhang which projects beyond the shell when the insert is received in the shell to reduce the likelihood of dislocation of the femoral head; and
   interlocking means on said surface of the shell at said inner opening and on the polar cap of the insert for holding the insert in any of a plurality of different angular positions relative to the shell whereby a desired angular orientation of the overhang can be selected.

2. An acetabular cup as defined in claim 1 wherein said interlocking means includes a plurality of interlockable gear teeth on said surface of the shell surrounding the inner opening and around the periphery of the polar cap of the insert.

3. An acetabular cup as defined in claim 1 wherein the shell has at least one port leading to said cavity.

4. An acetabular cup as defined in claim 1 wherein said shell has a part spherical outer surface which extends for no more than a hemisphere and said inner opening is at a polar region of the shell.

5. An acetabular cup as defined in claim 1 wherein said overhang extends circumferentially for no more than about 180°.

6. An acetabular cup as defined in claim 1 wherein the center of the bearing surface is substantially at the center of the acetabulum when the shell and insert are implanted in the acetabulum.

7. An acetabular cup as defined in claim 1 including means for releasably locking the insert into the shell.

8. An acetabular cup as defined in claim 1 wherein said interlocking means includes a plurality of interlockable gear teeth, said shell has a plurality of ports leading to said cavity and a part spherical surface which extends for no more than a hemisphere.

9. An acetubular cup as defined in claim 1 including indicia on the shell and the insert for correlating the anular position of the insert relative to the shell.

10. An acetubular cup as defined in claim 2 including first indicia on the shell in radial alignment with alternate teeth of the shell and second indicia different from the first indicia in radial alignment with the other teeth of the shell and third indicia on the insert in radial alignment with one of the teeth of the insert.

11. An acetabular cup as defined in claim 1 wherein said shell has a part spherical outer surface and the center of said part spherical outer surface coincides with the center of said baring surface when the insert is received within the shell.

12. An acetabular cup which can be implanted in the acetabulum comprising:

a shell having inner and outer ends, a cavity having an outer opening at said outer end and external screw threads for threading the shell into the acetabulum by rotation of the shell generally about a rotational axis which extends between said inner and outer ends;

driven surface means on said shell for cooperating with a tool to screw the shell into the acetabulum;

an insert having a concave bearing surface of generally part-spherical configfuration opening at a mouth, said bearing surface being adapted to receive a femoral head and slidably cooperate therewith, said insert being receivable in the cavity of the shell;

said insert having an overhang which projects beyond the shell when the insert is received in the shell to reduce the likelihood of dislocation of the femoral head;

interlocking means on said insert and said driven surface means for holding the insert in any of a plurality of different angular positions relative to the shell whereby a desired angular orientation of the overhang can be selected; and the shell and insert each have polar regions and said interlocking means and said driven surface means are at the polar regions of the shell and the insert, respectively.

13. An acetabular cup as defined in claim 12 wherein said driven surface means defines an inner opening at the polar region of the shell.

14. An acetabular cup as defined in claim 1 wherein the polar cap of the insert is generally gear-shaped and said interlocking means includes the periphery of the gear-shaped polar cap.

15. An acetabular cup as defined in claim 1 wherein the shell has an end wall at said inner end and said surface defines said inner opening in said end wall, said insert has a shoulder engageable with the end wall when the insert is received in the cavity of the shell and asid polar cap projects from said shoulder.

16. An acetabular cup as defined in claim 15 wherein said interlocking means includes a plurality of interlockable gear teeth on the shell and the insert.

* * * * *